United States Patent
Tian et al.

(10) Patent No.: US 8,810,568 B2
(45) Date of Patent: Aug. 19, 2014

(54) METHODS AND APPARATUSES FOR CREATING ORIENTATION MARKERS AND 3D ULTRASOUND IMAGING SYSTEMS USING THE SAME

(75) Inventors: Yong Tian, Shenzhen (CN); Bin Yao, Shenzhen (CN); Yue She, Shenzhen (CN)

(73) Assignee: Shenzhen Mindray Bio-Medical Electronics Co., Ltd, Shenzhen (CN)

( * ) Notice: Subject to any disclaimer, the term of this patent is extended or adjusted under 35 U.S.C. 154(b) by 56 days.

(21) Appl. No.: 13/234,931

(22) Filed: Sep. 16, 2011

(65) Prior Publication Data

US 2012/0069010 A1   Mar. 22, 2012

(30) Foreign Application Priority Data

Sep. 17, 2010  (CN) .......................... 2010 1 0285284

(51) Int. Cl.
| | |
|---|---|
| *G06T 15/00* | (2011.01) |
| *G06T 19/00* | (2011.01) |
| *A61B 8/08* | (2006.01) |
| *A61B 8/00* | (2006.01) |

(52) U.S. Cl.
CPC ................ *A61B 8/466* (2013.01); *G06T 19/00* (2013.01); *A61B 8/52* (2013.01); *G06T 2210/41* (2013.01)

USPC .......................................................... 345/419

(58) Field of Classification Search
USPC .......................................................... 345/419
See application file for complete search history.

(56) References Cited

U.S. PATENT DOCUMENTS

| | | | |
|---|---|---|---|
| 2006/0100512 A1* | 5/2006 | Lee ............................... | 600/437 |
| 2007/0167760 A1* | 7/2007 | Kim et al. .................... | 600/437 |
| 2012/0007863 A1* | 1/2012 | Endo et al. .................... | 345/419 |

FOREIGN PATENT DOCUMENTS

| | | |
|---|---|---|
| CN | 1452940 A | 11/2003 |
| CN | 1010658431 A | 3/2010 |
| CN | 101770650 A | 7/2010 |
| JP | 2009011449 A | 1/2009 |
| JP | 200900167 A | 8/2009 |

OTHER PUBLICATIONS

Frank, R. J., H. Damasio, and T. J. Grabowski. "Brainvox: an interactive, multimodal visualization and analysis system for neuroanatomical imaging." Neuroimage 5.1 (1997): 13-30.*
"Brainvox: A Preliminary User's Guide." NITRC. N.p., n.d. Web. Apr. 1, 2013. <www.nitrc.org/docman/view.php/311/720/>.*

* cited by examiner

*Primary Examiner* — David Zarka
*Assistant Examiner* — Vu Nguyen
(74) *Attorney, Agent, or Firm* — Kory D. Christensen; Stoel Rives LLP

(57) ABSTRACT

Methods and systems for creating an orientation marker in a 3D ultrasound imaging system are disclosed.

17 Claims, 5 Drawing Sheets

METHODS AND APPARATUSES FOR CREATING ORIENTATION MARKERS AND 3D ULTRASOUND IMAGING SYSTEMS USING THE SAME

CROSS-REFERENCE TO RELATED APPLICATIONS

This application claims the benefit of Chinese Patent Application No. 201010285284.5, filed on Sep. 17, 2010, which is incorporated herein by reference.

TECHNICAL FIELD

The following disclosure relates to 3D ultrasound imaging.

SUMMARY OF THE INVENTION

Disclosed herein are methods and systems for creating orientation markers for 3D ultrasound imaging.

DETAILED DESCRIPTION

Conventional ultrasound imaging devices can only provide two-dimensional images of the human body. As a result, the sizes and shapes of lesions can only be empirically estimated by doctors based on a plurality of two-dimensional images. The three-dimensional geometry of a lesion and its surrounding tissues must be imagined by the doctor, leading to difficulties in diagnosis. With the application of 3D visualization technology in ultrasound imaging systems, diagnosis has become more accurate. For example, a 3D image may be reconstructed based on a series of two-dimensional images and then displayed on a monitor. Not only the overall visual construction of the imaging object may be obtained from the 3D image, but also a significant amount of important 3D information may be saved. Accordingly, 3D ultrasound imaging devices have been widely used in recent years because of their non-destructive, radiationless, and highly flexible operation in clinical practice.

3D ultrasound imaging systems can obtain 3D images and section images of an imaging object. These 3D images and section images may be displayed using 3D views and section views on the display screen of the 3D ultrasound imaging system. Usually, the 3D ultrasound imaging system allows users to interact with the obtained 3D views and section views, including rotating, zooming, translating, switching between views, and adjusting positions of views, etc. After interaction, the 3D views and the section views will be located at a special spatial position relationship. The user must be able to identify the spatial position relationship of the 3D views and the section views; otherwise the contents of the views cannot be understood accurately, which leads to ineffective diagnosis. It is usually very difficult for users to identify the spatial position relationship by identifying the contents of the 3D views and the section views or by remembering the operation path.

The present disclosure provides for accurate, visual, and vivid "maps" displayed on the screen together with the 3D views and section views to help the users to identify the spatial position relationship of the 3D views and section views. Hereinafter, these kinds of "maps" are referred to as "orientation markers."

Figure 1:
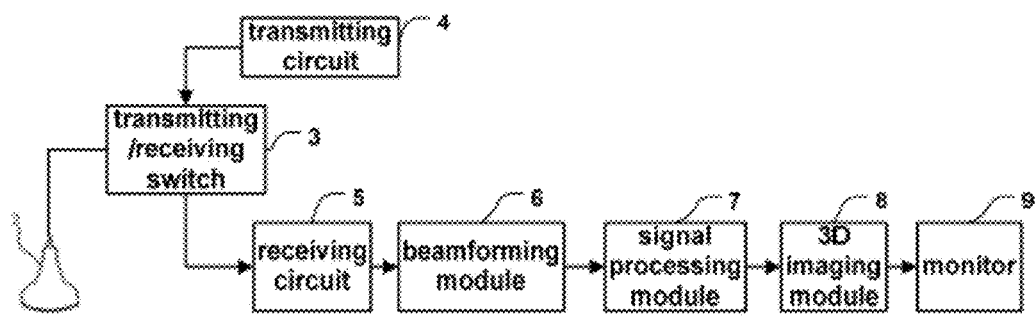
FIG. 1 is a block diagram of a 3D ultrasound imaging system.

Referring to FIG. 1, a 3D ultrasound imaging system may include a probe 2, a transmitting/receiving switch 3, a transmitting circuit 4, a receiving circuit 5, a beam-forming module 6, a signal processing module 7, a 3D imaging module 8, and a monitor 9. In one embodiment, the transmitting circuit 4 sends a group of pulses, which have been focused with time delays, to the probe 2. The probe 2 emits ultrasound waves to the tissues to be imaged (not shown), receives ultrasound echoes reflected from the tissues that carry tissue information, and converts the ultrasound echoes to electrical signals. The receiving circuit 5 receives these electrical signals and transmits them to the beam forming module 6. After time delay focusing, weighting, and channel summation processing in the beam forming module 6, those signals are transmitted to the signal processing module 7 for signal processing. Thereafter, the signals are sent to the 3D imaging module 8 for 3D imaging processing. Finally, the 3D images with other visual information are transmitted to the monitor 9 for display.

Figure 2:
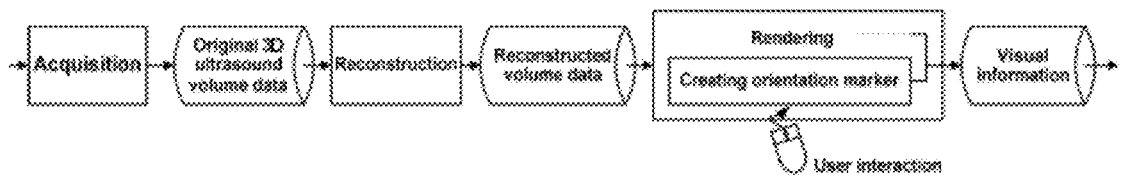
FIG. 2 is a flow-chart of a 3D imaging process.

As shown in FIG. 2, a processing method performed by the 3D imaging module 8 may includes three steps: acquisition, reconstruction, and rendering. In the acquisition step, the original 3D ultrasound volume data are obtained. There are typically two ways to obtain the original 3D volume data. The first is using free hand scanning and acquiring the 3D volume data offline. The second is using a special volume-scanning probe, which can obtain real time 3D volume data.

In the reconstruction step, the original volume data are converted into reconstructed volume data in rectangular coordinates, which have relative positions corresponding to that of the real space. Thus, in the rendering step, accurate images without distortion can be obtained.

In the rendering step, the reconstructed volume data are processed with a visual algorithm to obtain visual information (e.g., 3D images), and the visual information is displayed on a monitor.

The original volume data are acquired in the acquisition step, after which the original volume data are converted into reconstructed volume data in the reconstruction step. Thereafter, the reconstructed volume data are calculated and processed with possible user interaction to obtain the visual information.

In one embodiment, the acquisition step, the reconstruction step, and the rendering step set forth above may be carried out using the ordinary methods in the art and will not be discussed in greater detail here.

In the 3D ultrasound imaging process, the entire space region is typically scanned, including the imaging target, to obtain the information about the tissue or other targets (organs, blood, etc.) in the target space region. The space region is referred to herein as the "ultrasound imaging space."

In one embodiment, the 3D images are displayed in the 3D views, and the section images are displayed in the section views. A vector may be defined that is perpendicular to a view and points forward as a "viewing direction" of the view. For the 3D views, the viewing directions are "3D viewing directions." For the section views, the viewing directions are "section viewing directions". In certain embodiments, one 3D view and three sections views may be displayed on the monitor 9 at the same time, and the viewing directions of the three section views may be perpendicular to each other. In addition, one viewing direction of the three section viewing directions may be parallel with the 3D viewing direction, and the other two may be perpendicular to the 3D viewing direction. In other embodiments, more arbitrary 3D views and/or more arbitrary section views may be displayed on the monitor 9 at the same time, and the viewing directions of them may be not parallel with and/or perpendicular to each other.

The 3D ultrasound imaging system described above may provides accurate, intuitive, and vivid orientation markers to help users identify the spatial position relationship of current 3D views and section views. Therefore, the rendering step may further include steps for creating orientation markers according to scanning parameters determined in the acquisition step, initial 3D viewing directions and section viewing directions, or 3D interaction information and section interaction information generated by interaction with the user, etc. Thereafter, the created orientation markers are displayed on the monitor 9 together with the 3D views and section views.

Figure 3:
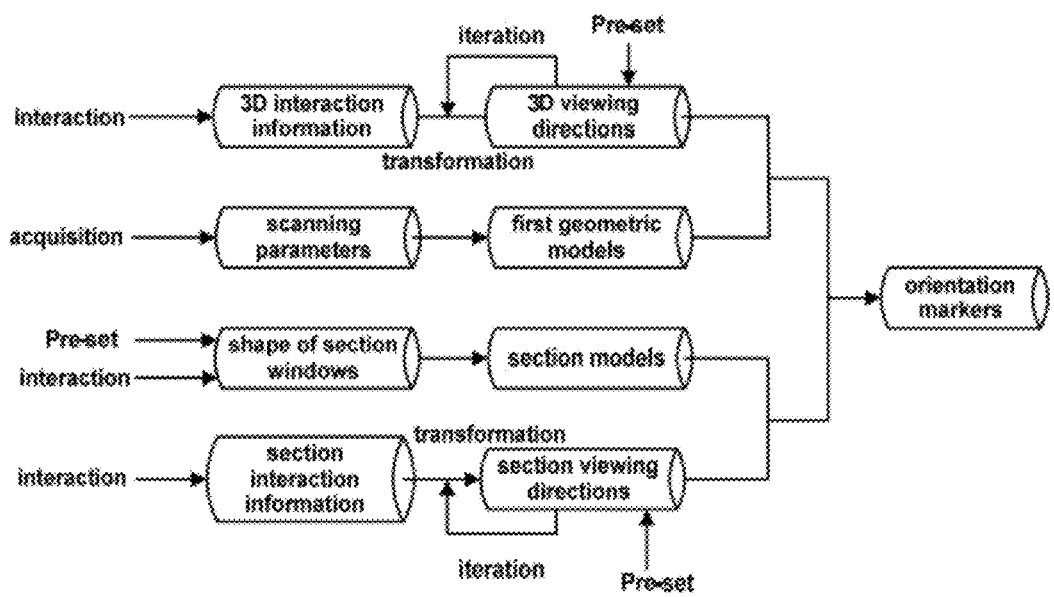
FIG. 3 is a flow-chart illustrating a method for creating orientation markers.

As shown in FIG. 3, a method for creating orientation markers according to an embodiment of this disclosure includes: modeling according to scanning parameters to build a first geometric model representing the ultrasound imaging space; determining the 3D viewing directions and the section viewing direction; building a section geometric model representing a section view in which a section image is displayed; drawing a first geometric model according to the 3D viewing directions, and drawing the section geometric model according to the section viewing direction, wherein spatial position relationships between the first geometric model and the section geometric model are the same as the spatial position relationships between the ultrasound imaging space and the section image.

The steps will be described hereafter in greater detail.

Step 1: Modeling According to Scanning Parameters to Build a First Geometric Model Representing the Ultrasound Imaging Space.

Figure 4:
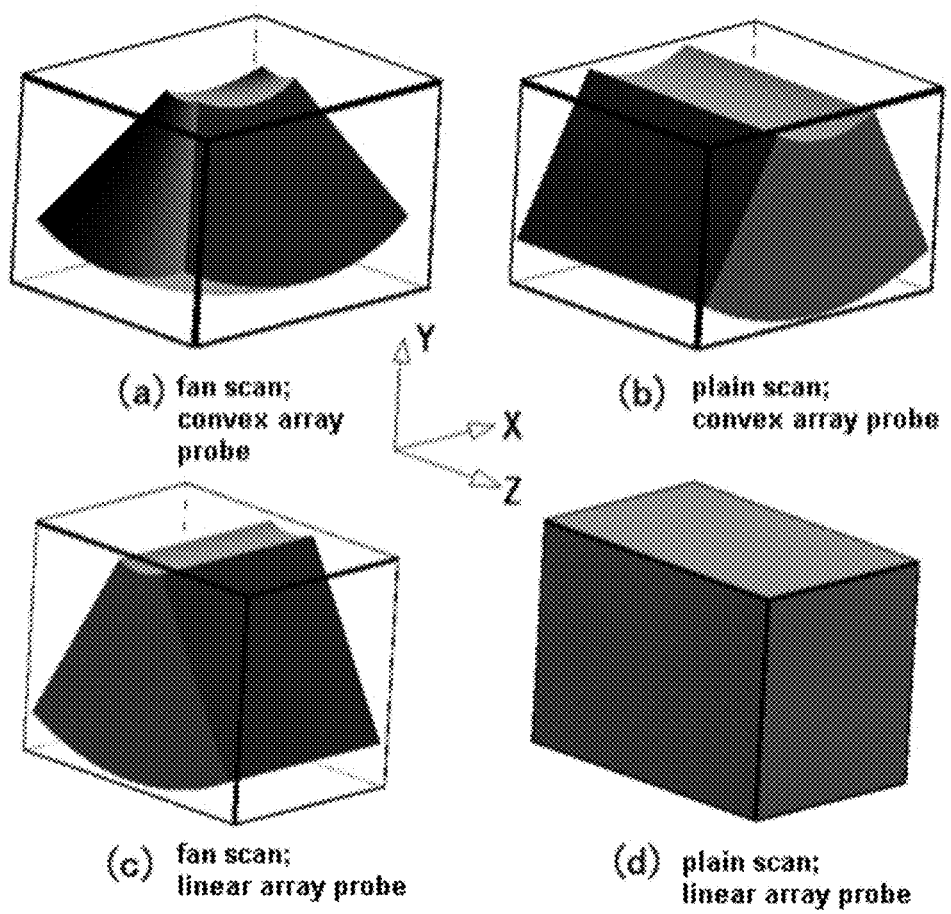
FIG. 4 is a schematic diagram of ultrasound imaging spaces.

In the reconstruction step, the original volume data are converted into reconstructed volume data. The frame in FIG. 4 represents the reconstructed volume data. The effective data among the reconstructed volume data constitute a geometric solid with a special shape representing the actual ultrasound imaging space, as shown by the geometric solid within the frame in FIG. 4. For different scanning modes, the shapes of the geometric solids are different. A geometric solid may be expressed by a geometric model (hereinafter referred to as "first geometric model") that is based on the scanning parameters determined by the system or user interaction when scanning is being carried out in the acquisition step.

For example, when the scanning mode is a plain scan using a convex array probe, the geometric solid is a cylinder having fan-shaped sections. The geometric solid has six surfaces, four of which are planes and two of which are cylindrical surfaces. The first geometric model representing this geometric solid may be obtained by calculating the equations of these surfaces using the scanning parameters.

The first geometric model representing the geometric solid may be obtained by modeling using the scanning parameters. The first geometric model may include six surfaces. For different scanning modes, the types of the surfaces are different, for example, as shown in Table. 1.

TABLE 1

Types of Surfaces of the First Geometric Model

| Position/ Mode | Fan scan with convex array probe | Plain scan with convex array probe | Fan scan with linear array probe | Plain scan with linear array probe |
|---|---|---|---|---|
| Top surface and bottom surface | Anchor ring | Circular cylindrical surface | Circular cylindrical surface | Plane |
| Left surface and right surface | Circular conical surface | Plane | Plane | Plane |
| Front surface and real surface | Plane | Plane | Plane | Plane |

The first geometric model representing the geometric solid may be obtained by calculating the equations of these surfaces using the scanning parameters. The methods for calculating the equations of these surfaces using the scanning parameters may be ordinary methods in the art and will not be described in detail here.

The first geometric model obtained may be used as the main portions of the orientation markers. Accordingly, the main portions of the orientation markers represent the actual ultrasound imaging space, which will show the spatial position relationship of the 3D views and the section views more accurately.

Step 2: Determining the 3D Viewing Directions and the Section Viewing Directions.

In certain embodiments, one 3D view and three section views may be displayed on the monitor 9 at the same time, each of which has a viewing direction. To determine the 3D viewing direction and the section viewing directions, it may be necessary to show the locations of the 3D view and the section views and the relationship therebetween in the orientation markers.

As set forth above, a viewing direction may be a vector that is perpendicular to the view and points forward. The initial 3D viewing directions and initial section viewing directions may be obtained. The initial viewing directions may be set by the 3D ultrasound imaging system or by user interaction. The viewing directions may be expressed by vectors or corresponding viewing coordinate systems, which are referred to as the "3D viewing coordinate system" and the "section viewing coordinate system."

The 3D viewing coordinate system may be built up based on the coordinate system of the first geometric model. For example, the 3D viewing coordinate system may be built by defining the origin of the coordinate system of the first geometric model as the origin, the –Z direction of the coordinate system of the first geometric model as the X direction, the –X direction of the coordinate system of the first geometric model as the Y direction, and the Y direction of the coordinate system of the first geometric model as the Z direction. The Z direction may then be the 3D viewing direction.

In other embodiments, the 3D viewing coordinate system may be built up independently according to actual conditions rather than being based on the existing coordinate system.

After the 3D viewing coordinate system is built up, the 3D viewing direction may be the Y direction, the Z direction, the –X direction, the –Y direction, the –Z direction, or other directions of the 3D viewing coordinate system, which may be set according to actual conditions.

Similarly, the section viewing coordinate system may be built up based on the coordinate system of the first geometric model or the 3D viewing coordinate system, or may be built up independently. For example, the section viewing coordinate system may be built up as follows:

a) build the section viewing coordinate system of the first section view by defining the origin of the 3D viewing coordinate system as the origin, the −Y direction of the 3D viewing coordinate system as the X direction, the Z direction of the 3D viewing coordinate system as the Y direction, and the X direction of the 3D viewing coordinate system as the Z direction;

b) build the section viewing coordinate system of the second section view by defining the origin of the 3D viewing coordinate system as the origin, the X direction of the 3D viewing coordinate system as the X direction, the Z direction of the 3D viewing coordinate system as the Y direction, and the Y direction of the 3D viewing coordinate system as the Z direction;

c) build the section viewing coordinate system of the third section view by defining the origin of the 3D viewing coordinate system as the origin, the Y direction of the 3D viewing coordinate system as the X direction, the −X direction of the 3D viewing coordinate system as the Y direction, and the Z direction of the 3D viewing coordinate system as the Z direction.

After the section viewing coordinate system is built up, the section viewing direction may be the Y direction, the Z direction, the −X direction, the −Y direction, the −Z direction, or other directions of the section viewing coordinate system, which may be set according to actual conditions.

In 3D ultrasound imaging, users may "operate" (interact with) the 3D views and/or the section views, including rotating, zooming, translating, switching between views, and adjusting positions of views, etc. Such operation is referred to as "user interaction" in this disclosure. The user interaction will make the 3D viewing directions and/or the section viewing directions change. Therefore, to update the 3D viewing directions and/or the section viewing directions according to 3D interaction information and/or section interaction information generated by user interaction, it may be necessary to obtain current 3D viewing directions and/or current section viewing directions. For example, vectors expressing the viewing directions may be continually updated according to 3D interaction information and/or section interaction information generated by user interaction to obtain current vectors, and the 3D viewing coordinate system and/or the section viewing coordinate system may be continually updated according to 3D interaction information and/or section interaction information generated by user interaction to obtain the current 3D viewing coordinate system and/or the current section viewing coordinate system. As users operate the views, the viewing directions may be updated continually in real time.

In one embodiment, the user interaction may be synchronal. That is, an operation to one view will affect the other views. For example, if the section viewing coordinate system was built up based on the 3D viewing coordinate system and the relationship between them did not change, changing the 3D viewing direction will make the section viewing directions change correspondingly. In another embodiment, the user interaction may be independent. That is, an operation to one view will not affect the other views. For example, if the section viewing coordinate system was built up based on the coordinate system of the first geometric model, changing the 3D viewing direction may not affect the section viewing direction.

Step 3: Building a Section Geometric Model Representing a Section View in which a Section Image is Displayed.

As set forth above, there are typically one 3D view and several (usually three) section views, nine of which are displayed on the monitor at the same time. The section images are displayed in the section views. In an embodiment of the 3D ultrasound imaging system of this disclosure, the section views are windows displayed on the screen of the monitor 9. These windows are referred to herein as "section windows." The shapes of the section windows are not limited and may be set according to actual conditions. For example, the shapes of the section windows may be rectangular, fan-shaped, circular, polygonal, etc.

In 3D ultrasound imaging, when the section images are currently displayed and the shape of the section windows are determined, the spatial position relationship (e.g., relative position relationship, relative size relationship, etc.) between current section images and current 3D images or 3D views or between current section views and current ultrasound imaging space are determined. Therefore, in one embodiment, the parameters related to the shape and size of the section windows and the spatial position relationship between current section windows and current 3D views may be obtained directly from the 3D imaging process set forth above. In other embodiments, these parameters may be set by the 3D ultrasound imaging system or the user. In this disclosure, the parameters related to the shape and size of the section windows and the spatial position relationship between current section windows and current 3D views are referred to as "section parameters."

First, the shapes of the section windows are obtained. Then, the section geometric models may be built up based on the shapes of the section windows. Building the section geometric model means expressing the section windows in a pre-set coordinate system. This may include, for example, obtaining equations of the sides of the section windows in the pre-set coordinate system. In this disclosure, the pre-set coordinate systems are referred to as "section model coordinate systems." The section model coordinate systems may be set according to actual conditions. For example, the section model coordinate systems may be set the same as the section viewing coordinate system, or may be set in other ways.

In one embodiment, the shape of the section windows may be rectangular. The size of the section windows may be expressed using pixels, e.g., 400 pixels×300 pixels, or using physical length, e.g., 40 mm×30 mm. The actual size of the section windows may be converted into the size of the section geometric model representing the section windows in the section model coordinate systems in a certain proportion. The proportion may be set by the 3D ultrasound imaging system or the user according to actual requirements. For example, for the 400 pixels×300 pixels or 40 mm×30 mm section window, the size of the section geometric model representing this section window may be 4 mm×3 mm. The equations of the four sides of the section geometric model in the section model coordinate system may be calculated according to the size of the section geometric model. For example, in one embodiment, if the section model coordinate system is the same as the section viewing coordinate system, the Z direction is the section viewing direction, the center of the section geometric model is located at the origin of the section model coordinate system, and the sides of the section geometric model are parallel with the axis of the section model coordinate system, then, in the section model coordinate system, the coordinates of the vertexes of the 4 mm×3 mm section geometric model mentioned above will be (−2.0, −1.5), (2.0, −1.5), (−2.0, 1.5) and (2.0, 1.5), and the equations of the sides of the section geometric model will be x=−2.0, y=−1.5, x=2.0, and y=1.5.

When the equations of the sides of the section geometric model are obtained, the section geometric model representing the section view is built up.

In various embodiments, the section windows may be other shapes, and the section model coordinate system may be built up in different ways. In these cases, the equations of the sides of the section geometric models in the section model coordinate system may be calculated based on the sizes of the section geometric models using mathematical methods, which are known in the art and will not be discussed in detail here.

As set forth above, the shape of the section windows or the section viewing directions may change based on user interaction. In such a case, the equations of the sides of the section geometric models may be calculated again to update the section geometric models.

After building the section geometric models, it is possible to visually and accurately represent the shape and position of the section views in the orientation markers.

Step 4: Combining the First Geometric Models and the Section Geometric Models to Obtain the Orientation Markers.

In above steps, the first geometric models, the section geometric models, the 3D viewing directions, and the section viewing directions may be obtained. And as set forth above, in 3D ultrasound imaging, when section images are currently displayed and the shape of the section windows are determined, the spatial position relationship (including relative position relationship and/or relative size relationship) between current section images and current 3D images or 3D views or between current section views and current ultrasound imaging space are determined. Therefore, the section parameters related to the shape and size of the section windows and the spatial position relationship between current section windows and current 3D views may be obtained directly from the 3D imaging process. The first geometric models and the section geometric models may be combined by drawing the first geometric model according to the 3D viewing direction and drawing the section geometric model according to the section viewing direction while making the spatial position relationships between the first geometric model and the section geometric to be the same as, or be corresponding to, the spatial position relationships between the ultrasound imaging space and the section views. In this way, the orientation markers, which include the first geometric models and the section geometric models having the same spatial position relationships as the ultrasound imaging space and the section views, are obtained.

The first geometric models and the section geometric models may be combined in the coordinate system of the first geometric models, the section model coordinate system, or a new coordinate system. The obtained orientation markers are drawn in these coordinate systems. In this disclosure, the coordinate systems in which the obtained orientation markers are drawn are referred to as the "orientation markers coordinate system." The orientation markers coordinate system may or may not be the same as the coordinate systems of the first geometric models or the section model coordinate system.

When the 3D viewing directions, the section viewing directions, the location of the section images, or the shape of the section windows change because of user interaction, the section geometric models may be updated, and the first geometric models and the updated section geometric models may be drawn again in real time according to the new 3D viewing directions, the new section viewing directions, or the new location of the section images, to update the orientation markers. Therefore, the orientation markers may be updated in real time with user interaction. Thereby the orientation markers may help the user identify the position of the 3D views and the section views during interacting.

Step 5: Displaying the Orientation Markers.

The orientation markers may be displayed on the monitor 9 for user viewing and identifying the position of the 3D views and the section views. The indication maps may be displayed together with the 3D views and the section views in the same interface or on the same monitor, or may be displayed separately with the 3D views and the section views.

In one embodiment, the orientation markers include the first geometric models and the section geometric models having the same spatial position relationships as the actual ultrasound imaging space and the actual section images. Therefore, the orientation markers may more accurately visually depict the actual ultrasound imaging space, the shape and position of the actual section images, and the spatial position relationship between the actual section images and the actual ultrasound imaging space.

Figure 5:
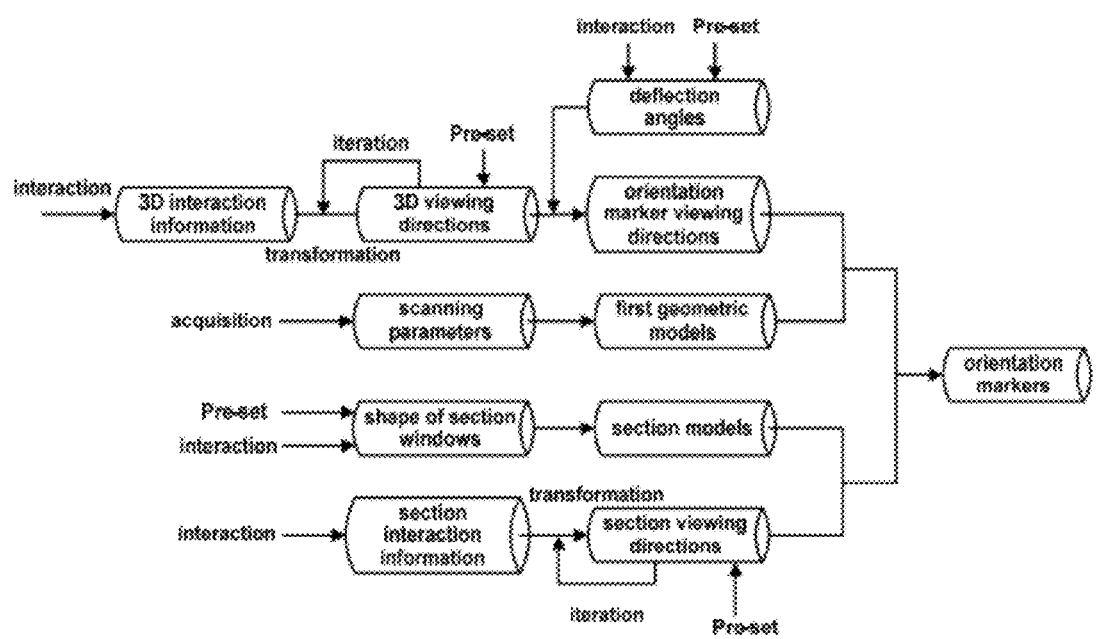
FIG. 5 is a flow-chart of a method for creating orientation markers.

In some embodiments, the method for creating orientation markers may further include a step 6 for determining an orientation marker viewing direction. FIG. 5 shows a flowchart of method for creating orientation markers. A deflection angle may be set by the 3D ultrasound imaging system or user, and an orientation marker viewing direction may be obtained by deflecting the 3D viewing direction through the deflection angle. The deflection angle may be a series of small angles. The deflection angle may be pre-set by the 3D ultrasound imaging system. For example, the 3D ultrasound imaging system may set the deflection angle to be 5 degrees to the right for the X direction, 5 degree up for the Y direction, and 0 degrees for the Z direction. In some embodiments, other small angles may be used, e.g., 0 to 10 degrees. The deflection angle may be set by user interaction. For example, users may rotate the 3D viewing directions to determine the deflection angle.

Similar to the 3D viewing directions or the section viewing directions, the orientation marker viewing directions may be expressed by vectors or viewing coordinate systems that are referred to as the "orientation marker viewing coordinate system" in this disclosure. The transformation relation between the 3D viewing coordinate systems and the orientation marker viewing coordinate systems, or between the vectors representing the 3D viewing directions and the vectors representing the orientation marker viewing directions, may be determined by the deflection angle. After obtaining the deflection angle, the orientation marker viewing coordinate systems or the vectors representing the orientation marker viewing directions may be obtained by coordinate transformation. The methods for the coordinate transformation may include methods known by a skilled artisan.

In one embodiment, after obtaining the orientation marker viewing directions, when combining the first geometric models and the section geometric models, the first geometric models will be drawn according to the orientation marker viewing directions, not the 3D viewing directions, to obtain the orientation markers.

The others steps of this embodiment are the same as the embodiments set forth above. Therefore, they are not described in detail here.

In 3D ultrasound imaging system, typically two of the three section views displayed on the monitor 9 have section viewing directions that are perpendicular to the 3D viewing direction. In other words, there are two section views that are parallel with the 3D viewing direction. Thus, if the orientation marker viewing directions are the same as the 3D viewing directions without deflection, the section geometric model of the section view whose section viewing direction is perpendicular to the 3D viewing direction would appear to be a line in the orientation markers. In this case, the information of the section view cannot be completely shown in the orientation markers, and there is no 3D effect. Thereby, the orientation markers would not assist in visualizing the section views.

In one embodiment, the orientation markers are created using the orientation marker viewing directions, which deflect small angles from the 3D viewing directions. Because the deflection angles are small, the orientation marker viewing directions and the 3D viewing direction are similar. Therefore, the expression of the 3D view in the orientation markers may be accurate and visual. Because the orientation marker viewing directions are not parallel with the section views (rather, there are small angles between them), the section geometric models may appear to be maps having a three-dimensional effect in the orientation markers. Thus, the expression of the section view in the orientation markers may be accurate and visual.

The method for creating the orientation markers may further include a step 7 for rendering the orientation markers. First, the materials (visual parameters) of the orientation markers may be determined, including color, texture, transparency, diffuse reflection coefficient, and specular reflection coefficient, etc. Different materials may be used for different surfaces of the orientation markers. For example, the section geometric model and each of the six surfaces of the first geometric model may each have one material that is different from the others. Alternatively, some surfaces may have the same material, while the material is different from that of other surfaces. The materials may be pre-set by the 3D ultrasound imaging system or determined by the user. For example, an editor for editing the materials of the orientation markers may be provided. Users may edit and determine the materials of the orientation markers using the editor. For example, the section geometric model and the surfaces of the first geometric model may be set to have different colors, which may make the indication maps more visual and vivid.

After the materials of the orientation markers are determined, then, the orientation markers may be rendered using methods for image rendering. The methods for image rendering herein include, but not limited to, ray tracing, hiding, texture mapping, lighting, radiometry equation and the composition of them. After being rendered, the orientation markers may be more visual and more vivid. Therefore, they can help user to identify the spatial position relationship of the 3D view and the section view more easily.

A system using the above-described methods for creating the orientation markers is now described. In one embodiment, the 3D imaging module 8 includes a reconstruction unit and a rendering unit. The reconstruction unit converts the original volume data acquired from polar coordinates into Cartesian coordinates to obtain reconstructed volume data. The rendering unit processes the reconstructed volume data with a visual algorithm to obtain visual information (e.g., 3D images and section images).

Figure 6:
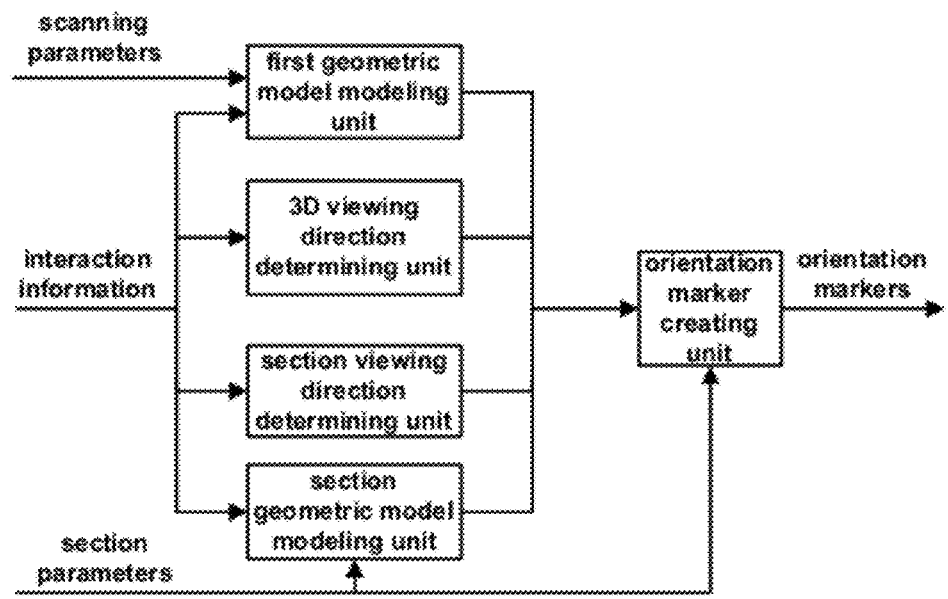
FIGS. 6 and 7 are block diagrams of systems for creating orientation markers.

In one embodiment, the 3D imaging module 8 further includes a system for creating orientation markers. As shown in FIG. 6, the system for creating orientation markers may include a 3D viewing direction determining unit, a first geometric model modeling unit, a section geometric model modeling unit, a section viewing direction determining unit, an orientation marker creating unit, and user interface unit (not shown).

The first geometric model modeling unit receives the scanning parameters determined during acquisition of the original volume data or determined by user interaction and models the data according to the scanning parameters to build the first geometric models representing the actual ultrasound imaging space. The first geometric model modeling unit includes a surface type determining sub-unit and a first calculating sub-unit. The surface type determining sub-unit determines the type of the surfaces of the first geometric model according to the scanning parameters. The first calculating sub-unit calculates the equations of the surfaces of the first geometric model according to the type of the surfaces and the scanning parameters. The first geometric model modeling unit may use the methods of step 1 above to build the first geometric models.

The 3D viewing direction determining unit determines the 3D viewing directions of the 3D views. The section viewing direction determining unit determines the section viewing directions of the section views. The 3D viewing direction determining unit may further include a first updating sub-unit. The first updating sub-unit receives the interaction information generated by users interaction with the 3D view and updates the 3D viewing directions according to the interaction information received. The section viewing direction determining unit may further include a second updating sub-unit, which receives the interaction information generated by the user interaction with the section view and updates the section viewing directions according to the interaction information received. The 3D viewing direction determining unit and the section viewing direction determining unit may use the methods of step 2 above to determine the 3D viewing directions and the section viewing directions.

The section geometric model modeling unit receives the section parameters of the section windows in which the section images are displayed and models the data according to the section parameters to build section geometric models representing the section views. The section geometric model modeling unit includes a shape determining sub-unit and a second calculating sub-unit. The shape determining sub-unit determines the shape of the section windows. The shape determining sub-unit may further include a shape updating sub-unit that receives the interaction information generated by user interaction with the shape of the section windows and updates the shape of the section windows according to the interaction information received. The second calculating sub-unit calculates the equations of the sides of the section geometric model according to the shape of the section windows to obtain the section geometric models. The section geometric model modeling unit may use the methods of step 3 above to build the section geometric models.

The orientation marker creating unit receives the section parameters representing the spatial position relationship between the section views and the 3D views or the ultrasound imaging space, draws the first geometric model according to the 3D viewing direction and draws the section geometric model according to the section viewing direction while making the spatial position relationships between the first geometric model and the section geometric model the same as, or correspond to, the spatial position relationships between the ultrasound imaging space and the section views to obtain the orientation markers. The orientation marker creating unit may use the methods of step 4 above to create the orientation markers.

Figure 7:
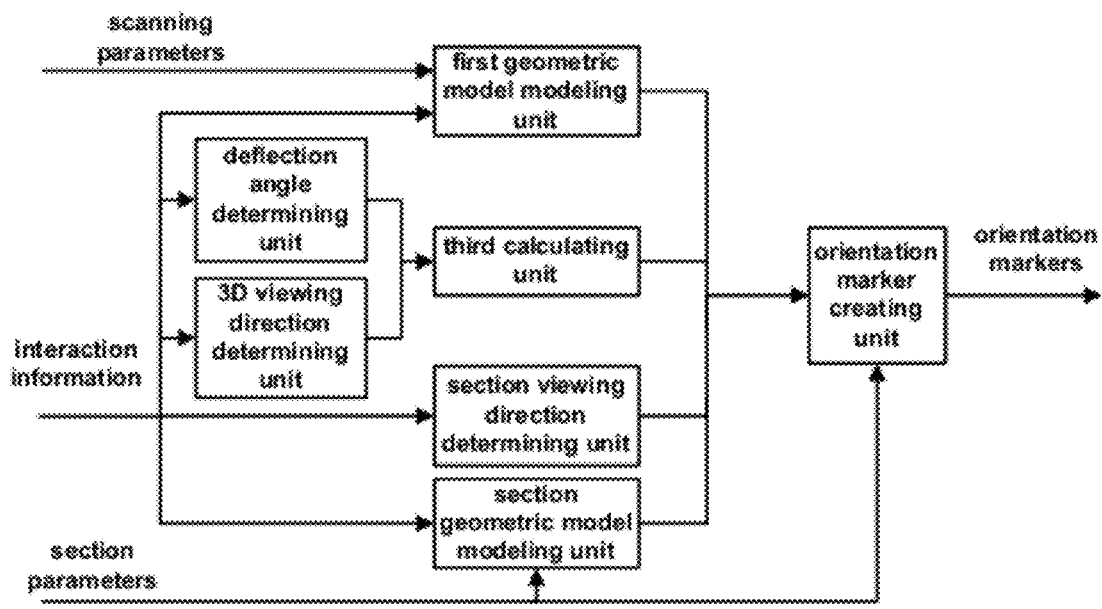

As shown in FIG. 7, in one embodiment, the system for creating orientation markers may further include a deflection angle determining unit and a third calculating unit. The deflection angle determining unit determines deflection angles relative to the 3D viewing directions. The third calculating unit calculates the orientation marker viewing directions based on the 3D viewing directions and the deflection angles. In this embodiment, the orientation marker creating unit draws the first geometric model according to the orientation marker viewing directions, as opposed to the 3D viewing directions, and draws the section geometric model according to the section viewing directions while making the spatial position relationships between the first geometric model and the section geometric the same as, or correspond to, the spatial position relationships between the ultrasound imaging space and the section views to obtain the orientation markers. The deflection angle determining unit and the third calculating unit may use the methods of step 6 above to obtain the deflection angles and the orientation marker viewing directions.

In some embodiments, the system for creating orientation markers may further include a rendering unit for determining the materials of the surfaces of the first geometric models and the section geometric models and rendering at least one of the surfaces of the first geometric models and the section geometric models using the materials.

Figure 8:
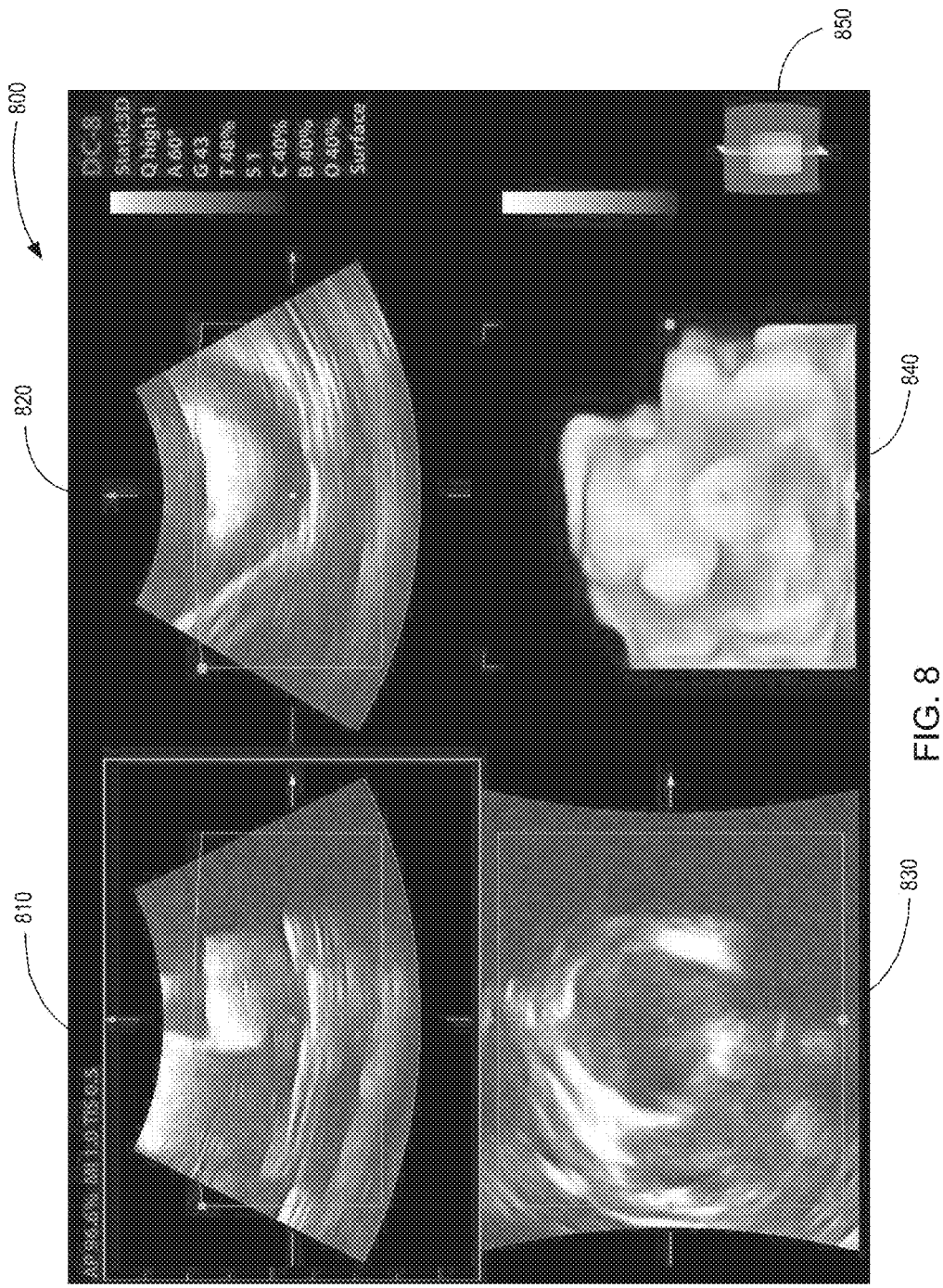
FIG. 8 is an exemplary display produced by a 3D ultrasound imaging system.

FIG. 8 is an exemplary display 800 produced by a 3D ultrasound imaging system. The display 800 may include three sectional views 810, 820, 830. The display also may include a 3D view 840. An orientation marker 850 may indicate the spatial position relationship between the 3D view 840 and the section views 810, 820, 830.

In the above description, numerous specific details are provided for a thorough understanding of the embodiments described herein. However, those of skill in the art will recognize that one or more of the specific details may be omitted, or other methods, components, or materials may be used. In some cases, operations or components are not shown or described where known to skilled artisans and/or to avoid obscuring more important details.

Furthermore, the described features, operations, or characteristics may be combined in any suitable manner in one or more embodiments. It will also be readily understood that the order of the steps or actions of the methods described in connection with the embodiments disclosed may be changed as would be apparent to those skilled in the art. Thus, any order in the drawings or Detailed Description is for illustrative purposes only and is not meant to imply a required order, unless specified to require an order.

Embodiments may include various steps, which may be embodied in machine-executable instructions to be executed by a general-purpose or special-purpose computer (or other electronic device). The general-purpose or special-purpose computer may include one or more general-purpose or special-purpose processors. Alternatively, the steps may be performed by hardware components that include specific logic for performing the steps or by a combination of hardware, software, and/or firmware.

Embodiments may also be provided as a computer program product including a non-transitory machine-readable medium having stored thereon instructions that may be used to program a computer (or other electronic device) to perform processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/machine-readable medium suitable for storing electronic instructions.

Those of skill in the art would further appreciate that the various illustrative logical blocks, modules, circuits, and algorithm steps described in connection with the embodiments disclosed herein may be implemented as electronic hardware, computer software, or combinations of both. To illustrate the interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the invention as claimed hereinafter.

What is claimed is:

1. A method for providing an orientation marker in a display of a three-dimensional (3D) ultrasound imaging system, the method comprising:
    obtaining scanning parameters;
    building a first geometric model representing an ultrasound imaging volume based on the scanning parameters;
    determining a 3D viewing direction of a 3D view;
    obtaining section parameters of a section window in which a section view is displayed;
    determining a section viewing direction of the section view;
    building a section geometric model based on the section parameters;
    obtaining the orientation marker by combining the first geometric model and the section geometric model while making a spatial position relationship between the first geometric model and the section geometric model the same as a spatial position relationship between the 3D view and the section view;
        wherein when the section geometric model becomes a line on the orientation marker, obtaining the orientation marker comprises
        determining one or more deflection angles relative to the 3D viewing direction;
        obtaining an orientation marker viewing direction by deflecting the 3D viewing direction with the one or more deflection angles, such that the orientation marker viewing direction is not parallel to the section viewing direction;
        drawing the first geometric model according to the orientation marker viewing direction; and
        drawing the section geometric model according to the section viewing direction while making the spatial position relationships between the first geometric model and the section geometric model the same as the spatial position relationships between the 3D view and the section view; and
    displaying the orientation marker.

2. The method of claim 1, wherein building a first geometric model representing an ultrasound imaging volume based on the scanning parameters comprises:
    determining one or more types of surfaces of the first geometric model according to the scanning parameters; and
    calculating equations of the surfaces of the first geometric model based on the one or more types of surfaces and the scanning parameters.

3. The method of claim 1, wherein building a section geometric model based on the section parameters comprises:
    determining a shape of the section window; and
    calculating equations of sides of the section geometric model based on the shape of the section window.

4. The method of claim 3, wherein determining the shape of the section window further comprises:
    receiving interaction information generated from user interaction with the shape of the section window; and updating the shape of the section according to the interaction information.

5. The method of claim 1, wherein determining a 3D viewing direction of a 3D view further comprises:
receiving interaction information generated from user interaction with the 3D view; and
updating the 3D viewing direction according to the interaction information.

6. The method of claim 1, wherein determining a section viewing direction of the section view comprises:
receiving interaction information generated from user interaction with the section view;
updating the section viewing direction according to the interaction information.

7. The method of claim 1, further comprising:
determining at least one material for rendering; and
rendering at least one surface of the first geometric model and the section model of the orientation marker using the material.

8. The method of claim 7, further comprising rendering at least two surfaces of the first geometric model and the section model of the orientation marker using different materials.

9. The method of claim 1, wherein determining the deflection angle relative to the 3D viewing direction comprises:
presetting the deflection angle by the 3D ultrasound imaging system; or
setting the deflection angle by interaction information generated from user interaction.

10. A three-dimensional (3D) ultrasound imaging system comprising:
a probe,
a signal processing module, and
one or more processors configured to:
obtain scanning parameters and build a first geometric model representing an ultrasound imaging volume based on the scanning parameters;
determine a 3D viewing direction of a 3D view;
obtain section parameters of a section window in which a section view is displayed and build a section geometric model based on the section parameters;
determine a section viewing direction of the section view;
obtain an orientation marker by combining the first geometric model and the section geometric model while making a spatial position relationship between the first geometric model and the section geometric the same as a spatial position relationship between the 3D view and the section view;
wherein when the section geometric model becomes a line on the orientation marker, the one or more processors are configured to:
determine one or more deflection angles relative to the 3D viewing direction;
obtain an orientation marker viewing direction by deflecting the 3D viewing direction with the one or more deflection angles, such that the orientation marker viewing direction is not parallel to the section viewing direction; and
further configured to draw the first geometric model according to the orientation marker viewing direction and draw the section geometric model according to the section viewing direction while making the spatial position relationship between the first geometric model and the section geometric the same as the spatial position relationships between the 3D view and the section view to obtain the orientation marker.

11. The system of claim 10, wherein the one or more processors are further configured to:
determine one or more types of the surfaces of the first geometric model according to the scanning parameters; and
calculate equations of the surfaces of the first geometric model based on the one or more types of the surfaces and the scanning parameters.

12. The system of claim 10, wherein the one or more processors are further configured to:
determine a shape of the section window; and
calculate equations of sides of the section geometric based on the shape of the section window.

13. The system of claim 12, wherein the one or more processors are further configured to:
receive interaction information generated from user interaction with the shape of the section view and update the section viewing direction according to the interaction information.

14. The system of claim 10, wherein the one or more processors are further configured to:
receive interaction information generated from user interaction with the 3D view and update the 3D viewing direction according to the interaction information.

15. The system of claim 10, wherein the one or more processors are further configured to:
receive interaction information generated from user interaction with the section view and update the section viewing direction according to the interaction information.

16. The system of claim 10, wherein the one or more processors are further configured to:
determine at least one material for rendering and render at least one surface of the first geometric model and the section model of the orientation marker using the at least one material.

17. A method for three-dimensional (3D) imaging in 3D ultrasound imaging system, the method comprising:
scanning an ultrasound imaging volume using scanning parameters to obtain original volume data;
reconstructing the original volume data and rendering reconstructed volume data to obtain 3D images and section images;
displaying the 3D images in 3D views;
displaying the section images in section views;
building a first geometric model representing the ultrasound imaging volume based on the scanning parameters;
determining a 3D viewing direction of the 3D view;
obtaining section parameters of a section window in which the section view is displayed;
determining a section viewing direction of the section view;
building a section geometric model based on the section parameters;
obtaining an orientation marker by combining the first geometric model and the section geometric model while making a spatial position relationship between the first geometric model and the section geometric the same as a spatial position relationship between the 3D view and the section view,
wherein when the section geometric model becomes a line on the orientation marker, obtaining the orientation marker comprises:
determining one or more deflection angles relative to the 3D viewing direction,
obtaining an orientation marker viewing direction by deflecting the 3D viewing direction with the one or more deflection angles, such that the orientation marker viewing direction is not parallel to the section viewing direction, drawing the first geometric model according to the orientation marker viewing direction, and drawing the section geometric model according to the section viewing direction while making the spatial position relationships between the first geometric model and the section geometric model the same as the spatial position relationship between the 3D view and the section view; and displaying the orientation marker.

\* \* \* \* \*